United States Patent
Adachi et al.

[11] 3,967,965
[45] July 6, 1976

[54] PHOTOGRAPHIC LIGHT-SENSITIVE MATERIAL CONTAINING ANTI-FOGGING AGENT

[75] Inventors: Keiichi Adachi; Akikazu Mikawa; Ikutaro Horie; Hisashi Shiraishi, all of Minami-ashigara, Japan

[73] Assignee: Fuji Photo Film Co., Ltd., Minami-ashigara, Japan

[22] Filed: Jan. 14, 1975

[21] Appl. No.: 540,764

[30] Foreign Application Priority Data
Jan. 14, 1974   Japan.................................. 49-7271

[52] U.S. Cl................................ 96/76 R; 96/95; 96/109
[51] Int. Cl.² ..................... G03C 1/48; G03C 1/06; G03C 1/34
[58] Field of Search............... 96/66.5, 95, 109, 76 R

[56] References Cited
UNITED STATES PATENTS

| | | |
|---|---|---|
| 2,324,123 | 7/1943 | Weissberger.......................... 96/109 |
| 3,023,103 | 2/1962 | Dersch et al.......................... 96/109 |
| 3,677,761 | 7/1972 | Brown et al. ......................... 96/66.5 |

*Primary Examiner*—Won H. Louie, Jr.
*Attorney, Agent, or Firm*—Sughrue, Rothwell, Mion, Zinn & Macpeak

[57]   ABSTRACT

A photographic light-sensitive material comprising a support having thereon at least one silver halide photographic emulsion layer and at least one of the layers of the photographic light-sensitive material containing a compound represented by the following general formula (I) or (II);

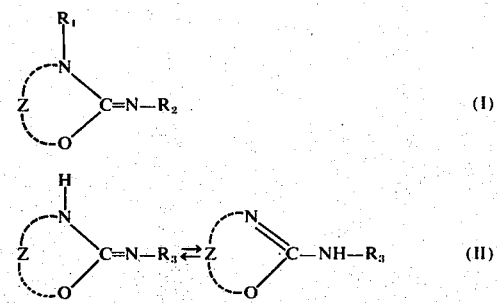

wherein $R_1$, $R_2$ and $R_3$ each represents a hydrogen atom, an alkyl group, an aryl group or a heterocyclic residue, or $R_1$ and $R_2$ can combine to form a ring; and Z represents an alkylene group; or an organic acid salt or a mineral acid salt of the compound represented by the general formula (I) or (II). The photographic material can be developed at an elevated temperature without fog information and a decrease in photographic sensitivity.

8 Claims, No Drawings

PHOTOGRAPHIC LIGHT-SENSITIVE MATERIAL CONTAINING ANTI-FOGGING AGENT

BACKGROUND OF THE INVENTION

1. Field of the Invention

The present invention relates to a silver halide light-sensitive material and, more particularly, it relates to a silver halide light-sensitive material in which fog occurs to a lesser extent.

2. Description of the Prior Art

As a method for rapidly processing light-sensitive materials, it is known to develop at an elevated temperature. In recent years, this method has been applied to the processing of various light-sensitive materials with some success. However, in general, development of light-sensitive materials at an elevated temperature tends to cause fog, which deteriorates the quality of the photographic images. (The term "elevated temperature" as used herein means a temperature of at least about 30°C.) In particular, when a developer containing a substance which has a hydrophilic colloid hardening action, for example, glutaraldehyde, etc., such as when a commercially available developer for rapidly processing X-ray films is used, films sometimes are fogged to a great extent by the developer, especially when the developer is exhausted or fatigued (i.e., when the amount of films processed approaches almost the limit of the processing capability of the developer).

In general, the photographic sensitivity of a photographic silver halide emulsion is enhanced by a sulfur compound, a reducing agent, a noble metal or a polyalkylene oxide compound. However, these sensitizing methods increase the fogging tendency as well as the photographic sensitivity. Therefore, various anti-fogging agents are added to photographic emulsions.

Typical examples of anti-fogging agents are 4-hydroxy-6-methyl-1,3,3a,7-tetraazaindene and 1-phenyl-5-mercaptotetrazole. The former compound markedly supresses increased fogging of light-sensitive materials or photographic emulsions during storage. However, this compound exhibits less of an anti-fogging effect in controlling fog immediately after the production of the light-sensitive material. On the other hand, the latter compound controls fog immediately after production. Therefore, favorable results are obtained by using these two compounds in combination.

However, when light-sensitive materials are processed at an elevated temperature, 4-hydroxy-6-methyl-1,3,3a,7-tetra-azaindene does not exhibit a marked fog controlling effect, while 1-phenyl-5-mercaptotetrazole, when used in a sufficient amount to control fog, deteriorates the sensitivity to such a marked degree that the use of this compound is not practical.

Thus, in elevated temperature development, it has been difficult to control fogging sufficiently using the aforesaid anti-fogging agents to the same extent as in ordinary development (such as is conducted at about 20°C).

SUMMARY OF THE INVENTION

Therefore, an object of the present invention is to provide a light-sensitive material which can be developed at an elevated temperature with sufficiently restrained fog formation and less reduction in sensitivity.

As a result of various investigations, it has now been found that a light-sensitive material which contains in a photographic layer and/or another hydrophilic colloid layer or layers (for example, an interlayer, a protective layer, and the like) at least one compound represented by the following general formulae;

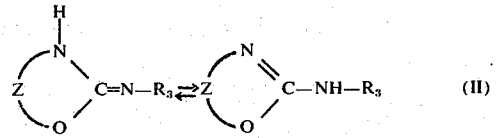

or an organic acid salt or a mineral acid salt (including inner salts) of the compound of the general formula (I) or (II) exhibits outstanding fog-controlling effects when the photographic material is processed at an elevated temperature with less reduction, if any, in sensitivity even if hardly any anti-fogging effects are exhibited when the photographic material is processed at temperatures used in ordinary development (at about 20°C). This phenomenon due to the addition of these compounds would not have been expected at all from conventional knowledge and is really a surprising discovery.

DETAILED DESCRIPTION OF THE INVENTION

In the above-described formulae, $R_1$, $R_2$ and $R_3$ each represents a hydrogen atom, an alkyl group (preferably an alkyl group having 12 or less carbon atoms, more particularly an alkyl group 1 to 6 carbon atoms; (for example, an unsubstituted alkyl group such as a methyl, ethyl, propyl, isopropyl, butyl, tertpentyl, etc. group); a cycloalkyl group (for example, a cyclohexyl group, etc.); a substituted alkyl group (such as an aralkyl group (for example, a benzyl group, a phenethyl group, etc.), an aminoalkyl group (for example, a diethylaminopropyl group, etc.) an alkoxyalkyl group (for example, a methoxyethyl group, etc.)), an aryl group (such as an unsubstituted phenyl group (for example, a phenyl group), an alkyl substituted phenyl group (for example a tolyl group), an alkoxy substituted phenyl group (for example a p-methoxyphenyl group) an N,N-dialkylaminophenyl group (for example, a p-N,N-dimethylaminophenyl group, etc.), and the like); a heterocyclic group (such as a 6-membered ring containing up to two nitrogen atoms and the remaining atoms being carbon atoms (for example, a pyridyl group, a pyrimidinyl group etc.), and the like); $R_1$ and $R_2$ can combine together through a dimethylene group or a methylenecarbonyl group, in which the methylene moiety in these groups can be substituted with an alkyl group containing 1 to 4 carbon atoms or a phenyl group; and Z represents an alkylene group having 2 to 4 carbon atoms (for example, an ethylene, propylene, 2-methylpropylene, butylene, etc. group).

The organic acids salts can be those of either aliphatic acids or aromatic acids (for example, p-toluenesulfonic acid, p-tert-butylbenzenesulfonic acid, oxalic acid, and the like) and the mineral acid salts can be those of hydrochloric acid, sulfuric acid, perchloric acid, etc.

Typical examples of the compounds which can be used in the present invention are set forth below.

1. 3-Cyclohexyl-2-(cyclohexylimino)oxazolidine oxalate
2. 3-Cyclohexyl-2-(cyclohexylimino)tetrahydro-1,3-oxazine oxalate
3. 3-Cyclohexyl-2-(cyclohexylimino)hexahydro-1,3-oxazepine oxalate
4. 3-Isopropyl-2-(isopropylimino)oxazolidine
5. 3-Isopropyl-2-(isopropylimino)tetrahydro-1,3-oxazine
6. 3-Isopropyl-2-(isopropylimino)hexahydro-1,3-oxazepine
7. 3-Isopropyl-2-(isopropylimino)-4-oxazolidone
8. 3-Isopropyl-2-(isopropylimino)-5-methyl-4-oxazolidone
9. 3-Isopropyl-2-(isopropylimino)oxazolidine hydrochloride
10. 3-Cyclohexyl-2-(cyclohexylimino)oxazolidine hydrochloride
11. 2-Phenylimino-3-methyl-1,3-oxazolidine
12. 2-Phenylimino-3-phenyl-1,3-oxazolidine
13. 5-Chloromethyl-3-isopropyl-2-isopropyliminooxazolidine
14. 5-Methyl-3-isopropyl-2-isopropyliminoxazolidine
15. 2,3-Dihydro-6,6-diphenylimidazo(2,1-b)oxazol-5-one
16. 2,3-Dihydro-6,6-dimethylimidazo(2,1-b)oxazol-5-one
17. 2-Phenyliminooxazolidine Methods for preparation of the compounds of the general formula (I) and (II) which can be used in the present invention are specifically illustrated below.

1. Synthesis of Compound (1)

A mixture of 41.2 g of dicyclohexylcarbodiimide and 7 g of ethylene glycol was heated on a water bath for 2 hours. After removing the precipitate of dicyclohexyl urea formed, the resulting oily product was dissolved in acetone and to the acetone solution was added an acetone solution containing 9 g of oxalic acid to obtain 35 g of Compound (1) with a melting point of 130° – 133°C.

2. Synthesis of Compound (2)

Compound (2) was obtained using the same procedure as described for Compound (1) using dicyclohexylcarbodiimide and trimethylene glycol. The melting point was 92° – 95°C.

3. Synthesis of Compound (3)

Compound (3) was obtained in the same manner as described above using dicyclohexylcarbodiimide and diethylene glycol. The melting point was 167° – 170°C.

4. Synthesis of Compound (4)

Compound (4) was obtained by the method described in Erich Schmidt and Wolfgang Karr; Ann., 685, 161 (1961). The boiling point was 86° – 87°C/9 mm Hg.

5. Synthesis of Compound (5)

Compound (5) was obtained in the same manner as described above for Compound (4) using trimethylene glycol. The boiling point was 94.5° – 95.5°C/9 mm Hg.

6. Synthesis of Compound (6)

Compound (6) was obtained in the same manner as described above for Compound (4) using diethylene glycol. The boiling point was 96° – 97°C/10 mm Hg.

7. Synthesis of Compound (7)

Compound (7) was obtained by the method described in Erich Schmidt and Wolfgang Karr; Ann., 639, 24 (1961). The boiling point was 96° – 98°C/10 mm Hg.

8. Synthesis of Compound (8)

Compound (8) was obtained by the method described in Schmidt etal, supra, for Compound (7). The boiling point was 92° – 94°C/11 mm Hg.

9. Synthesis of Compound (9)

Compound (9) was obtained by the method described in Schmidt etal, supra, in the synthesis of Compound (7). The melting point was 133° – 134°C.

10. Synthesis of Compound (10)

Compound (10) was obtained in the same manner as described above for Compound (7) using dicyclohexylcarbodiimide.

11. Synthesis of Compound (11)

Compound (11) was obtained by the method described in Hiroyuki Nohira, Yoshihiro Nishikawa and Teruaki Mukaiyama; Bull. Chem. Soc. Japan, 37, 797 (1964). The melting point was 74.5° – 75.5°C.

12. Synthesis of Compound (12)

Compound (12) was obtained by the method described in the Nohira etal, supra, for Compound (11). The melting point was 124°C.

13. Synthesis of Compound (13)

Compound (13) was obtained by the method described in E. Daebrity; Angew. Chem. Internat, Edit., 5, 470 (1966). The boiling point was 113° – 114°C/9 mm Hg.

14. Synthesis of Compound (14)

Compound (14) was obtained by the method described in Daebrity, supra, for Compound (13). The boiling point was 92° – 93°C/10 mm Hg.

15. Synthesis of Compound (15)

Compound (15) was obtained by the method described in Victor E. Marquez, Li-Ming Iwaumoh, Harry B. Wood Jr. and John S. Driscoll; J. Org. Chem., 37, 2558 (1972). The melting point was 188° – 190°C.

16. Synthesis of Compound (16)

Compound (16) was obtained by the method described in the Marquez et al, supra, for Compound (15).

17. Synthesis of Compound (17)

Compound (17) was obtained by the method described in Teruaki Mukaiyama, Tamotsu Fuzisawa, Hiroyuki Nohira and Teruo Hyugaji; J. Org. chem., 27, 3337 (1962). The melting point was 119° – 120°C.

The organic acid or mineral acid salts of the compounds of the general formulas (I) and (II) can easily be prepared by conversion of the corresponding free compound to the salt form. Such a conversion can be carried out, for example, by adding the organic acid or mineral acid to a solution of the compound of the general formulas (I) and (II).

The compound of the general formula (I) or (II) which can be used in the present invention can be added to a silver halide emulsion, preferably during chemical ripening or after chemical ripening, by dissolving the compound in water, or a water-miscible solvent such as methanol and the like. The compounds are added in a sufficient quantity to effectively prevent fog formation. The amount can suitably be determined by those skilled in the art depending upon the degee of ripening, kind of emulsion and the like. In general, a suitable amount in either the silver halide emulsion layer or a non-light-sensitive layer ranges from about 0.01 g to 50 g, preferably 0.5 to 5 g, per mol of silver halide.

Silver halide emulsions are usually prepared by mixing a solution of a water-soluble silver salt (for example, silver nitrate, etc.) with a solution of a water-soluble halide (for example, potassium bromide, etc.) in the presence of a solution of a water-soluble colloidal polymer such as gelatin. Particularly favorable results are obtained using silver bromoiodide and silver chlorobromoiodide as the silver halide. A more preferred silver halide is silver bromoiodide or silver chloromoiodide containing about 1 mol% to about 8 mol% silver iodide.

The form of the silver halide grains is not limited and they can be in a cubic form, octahedral form, a mixed form thereof, and the like.

These silver halide grains can be prepared according to conventional methods. For example, a single or twin jet method, a controlled jet method, or the like, can be suitably employed.

Also, two or more silver halide emulsions which have been prepared separately can be mixed with each other. Furthermore, with respect to the crystal structure of the silver halide grains, those grains in which the crystal structure is uniform, those grains in which the inner portion and the outer portion form a different stratum structure, or those grains of the so-called converted type as described in British Pat. No. 633,841 and U.S. Pat. No. 3,622,318 can all be suitably employed. Those emulsions in which latent images are mainly formed on the surface of the grains or those in which latent images are formed inside the grains (internal latent image type) are suitable also. These photographic emulsions are well known in the art, for example, as described in C.E.K. Mees & T.H. James; *The Theory of the Photograhic Process*, MacMillan Co. and Pierre Grafikides; *Photographic Chemistry*, Fauntain Press, and can be prepared according to various processes including an ammonia process, a neutral process, an acid process, and the like.

These silver halide grains can be washed after formation so as to remove water-soluble salts produced as a by-product (for example, potassium nitrate in the case of producing silver bromide using silver nitrate and potassium bromide) from the system and heat-processing them in the presence of a chemical sensitizer to increase the sensitivity without coarsening the grains. These general methods are also described in the above-described references.

Suitable hydrophilic collids which can be used (as a vehicle), include proteins such as gelatin, colloidal albumin, casein, and the like; cellulose derivatives such as carboxymethyl cellulose, hydroxyethyl cellulose, and the like; polysaccharides such as agar-agar, sodium alginate, starch derivatives, and the like; synthetic hydrophilic colloids such as polyvinyl alcohol, poly-N-vinylpyrrolidone, polyacrylic acid copolymers, polyacrylamide and derivatives thereof, and the like. If desired, a mixture of two or more of these colloids which are compatible with each other can be used. Of these, gelatin is the most commonly used. Part or all of the gelatin can be replaced by a synthetic polymer substance, by a gelatin derivative which is prepared by treating gelatin with a compound having a group capable of reacting with the functional groups in gelatin molecules such as, amino groups, imino groups hydroxy groups and carboxy groups, or by a graft polymer which is prepared by connecting or grafting molecular chains of other polymer substances with gelatin.

Suitable compounds which can be used to prepare the above-described gelatin derivatives include the isocyanates, the acid chlorides and the acid anhydrides as described in U.S. Pat. No. 2,614,928, the acid anhydrides as described in U.S. Pat. No. 3,118,766, the bromoacetic acids as described in Japanese Pat. Publication No. 5514/64, the phenyl glycidyl ethers as described in Japanese Pat. Publication No. 21845/67, the vinylsulfone compounds as described in U.S. Pat. No. 3,132,945, the N-allylvinylsulfonamides as described in British Pat. No. 861,414, the maleinimides as described in U.S. Pat. No. 3,186,846, the acrylonitriles as described in U.S. Pat. No. 2,594,293, the polyalkyleneoxides as described in U.S. Pat. No. 3,312,553, the epoxy compounds as described in Japanese Pat. Publication No. 26845/67, the acid esters as described in U.S. Pat. No. 2,763,639, and the alkanesultones as described in British Pat. No. 1,033,189, and the like.

Various kinds of polymers which can be grafted to gelatin, are set forth in U.S. Pat. Nos. 2,763,625, 2,831,767, 2,956,884, *Polymer Letters*, 5, 595 (1967), *Photo. Sci. and Eng.*, 9, 148 (1965), *J. of Polymer Sci.* A-1, 9, 3199 (1971), and the like. In general, polymers or copolymers of monomers, such as the so-called vinyl monomers, such as acrylic acid, methacrylic acid, or the ester, amide or nitrile derivatives thereof, styrene, and the like can be widely used. Of these, however, hydrophilic vinyl polymers having some compatibility with gelatin, such as the polymers or copolymers of acrylic acid, acrylamide, methacrylamide, hydroxyalkyl acrylates, hydroxyalkyl methacrylates, and the like are particularly desirable.

The compounds of the general formula (I) or (II) of the present invention are not affected by the copresence of photographic additives conventionally used such as stabilizing agents, hardening agents, coating aids, spectrally sensitizing agents, and the like.

That is, a hardening treatment of emulsions can be effected using conventional techniques. Examples of hardeners include, for example, formaldehyde, aldehyde compounds as described in U.S. Pat. No. 3,232,764, ketone compounds such as diacetyl, cyclopentanedione, etc.; compounds having a reactive halogen such as bis(2-chloroethylurea), 2-hydroxy-4,6-dichloro-1,3,5-triazine, and those described in U.S. Pat. No. 3,288,775, 2,732,303, British Pat. Nos. 974,723, 1,167,207, etc.; compounds having a reactive olefin group such as divinylsulfone, 5-acetyl-1,3-diacryloylhexahydro-1,3,5-triazine, and those described in U.S. Pat. Nos. 3,635,718, 3,232,763, British Pat. No. 994,869, etc.; N-methylol compounds such as N-hydroxymethylphthalimide and those described in U.S. Pat. Nos. 2,732,316, 2,586,168, etc.; isocyanates as described in U.S. Pat. No. 3,103,437; aziridine compounds as described in U.S. Pat. Nos. 3,017,280 and 2,983,611; acid derivatives as described U.S. Pat. Nos. 2,725,294 and 2,725,295; carbodiimide compounds as described in U.S. Pat. No. 3,100,704; epoxy compounds as described in U.S. Pat. No. 3,091,537; isoxazole compounds as described in U.S. Pat. Nos. 3,321,313 and 3,543,292; halogenocarboxyaldehydes such as mucochloric acid, etc.; dioxane derivatives such as dihydroxydioxane, dichlorodioxane, etc.; inorganic hardening agents such as chromium alum, zirconium sulfate, etc.

Also, precursors of the above-described compounds such as alkali metal bisulfite-aldehyde adducts, hydantoin methylol derivatives, primary aliphatic nitro alcohols, and the like can be used in place of the above-described compounds.

Conventionally employed chemical sensitizing methods can be applied to the silver halide emulsion which can be used in the present invention such as gold sensitization (for example, as described in U.S. Pat. Nos. 2,540,085, 2,597,856, 2,597,915, 2,399,083, etc.), sensitization with Group VIII metal ions, sulfur sensitization (for example, as disclosed in U.S. Pat. Nos. 1,574,944, 2,278,947, 2,440,206, 2,410,689, 3,189,458, 3,415,649, etc.), reduction sensitization (for example, as disclosed in U.S. Pat. Nos. 2,518,698, 2,419,974, 2,983,610, etc.), or a combination of these methods.

Specific examples of chemical sensitizing agents are sulfur sensitizing agents such as allylthiocarbamide, thiourea, sodium thiosulfate, cystine, etc.; noble metal sensitizing agents such as potassium chloroaurate, aurous thiosulfate, potassium chloropalladate, etc.; reduction sensitizers such as stannic chloride, phenylhydrazine, reductone, etc. Also, the emulsion can contain sensitizers such as polyoxyethylene derivatives, polyoxypropylene derivatives, derivatives having a quaternary ammonium group, etc., plasticizers for dimensional stability, latex polymers, and matting agents.

Furthermore, an antifogging agent such as nitrobenzimidazole, ammonium chloroplatinate, and the like, a stabilizer such as 4-hydroxy-6-methyl-1,3,3a,7-tetraazaindene, and the like can be incorporated in the emulsion. A coating aid such as saponin or sodium alkylbenzenesulfonate, and the like can also be present in the emulsion.

The photographic emulsion can be applied to a flexible support. Typical flexible supports include those which are conventionally used for photographic light-sensitive materials, such as cellulose nitrate films, cellulose acetate films, cellulose acetate butyrate films, cellulose acetate propionate films, polystyrene films, polyethylene terephthalate films, polycarbonate films, laminates thereof, thin glass films, and the like. A suitable coating amount can range from about 10 to 200 mg, preferably 50 to 200 mg, as silver halide per 100 cm$^2$ of the support, although this coating amount can vary depending on the end-use purpose, the kind of silver halide, the presence of photographic additives.

A transparent or opaque support can be selected as the support, depending upon the end-use purpose of the light-sensitive material. Also, in selecting a transparent support, colored transparent supports containing a dye or a pigment can be used as well as a colorless transparent supports. The use of colored transparent supports has been employed in X-ray films, and the like, and is described in the literature such as J. SMPTE, 67, 296 (1958), etc.

Opaque supports include those which do not completely intercept light such as ordinary papers, plastic films containing a white filler such as titanium dioxide and the like, or plastic films surface-treated according to a method as described in Japanese Pat. Publication No. 19068/72, and supports which completely intercept light such as papers and plastics containing carbon black, a dye, and the like.

Where the adhesivity between the support and the photographic emulsion layer is insufficient, a layer which has a good adhesivity to both of the support and the photographic emulsion layer can be provided as subbing layer. Also, in order to further improve the adhesiveness, the surface of the support can be subjected to a preliminary treatment such as a corona discharge, an ultraviolet light-irradiation, a flame treatment, and the like. The present invention is preferably applied to an emulsion for X-ray films.

A developer which can be used for a rapid processing at an elevated temperature preferably contains a hardener of the glutaraldehyde series. Rapid processing at an elevated temperature is well known in the art and is described in, e.g., U.S. Pat. No. 3,677,761.

The present invention will now to illustrated in greater detail by reference to the following examples. Unless otherwise indicated, all parts, percents, ratios and the like.

EXAMPLE 1

To 1 Kg of a gelatino-silver bromoiodide emulsion containing 1.5 mol% of silver iodide and having been subjected to sulfur sensitization and gold sensitization, 10 cc of a 1% solution of 4-hydroxy-6-methyl-1,3,3a,7-tetraazaindene, 30 cc of 10% saponin and 20 cc of 1% mucochloric acid were added. The resulting emulsion was divided into 7 equal portions. One portion was used as a control. To the remaining portions were added, respectively, a compound as set forth in Table 1. Each of the resulting emulsion portions was coated on a polyester base in a silver amount of 50 mg/100 cm$^2$ and dried to prepare samples. The thus prepared samples were exposed using a NSG II-type sensitometer and developed using the following developers. The results shown in Table 1 were obtained.

Developer (I)
| 1-Phenyl-3-pyrazolidone | 0.5 g |
| Sodium Sulfite (anhydrous) | 70 g |
| Hydroquinone | 9 g |
| Sodium Carbonate (monohydrate) | 35 g |
| Sodium Bromide | 5 g |
| Water to make | 1 liter |

Developer (II)
| Sodium Sulfite | 40 g |
| Hydroquinone | 25 g |
| Boric Acid | 10 g |
| 1-Phenyl-3-pyrazolidone | 1.5 g |
| Potassium Hydroxide | 30 g |
| 5-Methylbenzotriazole | 0.15 g |
| Glutaraldehyde Bisulfite | 15 g |
| Acetic Acid | 12 g |
| Potassium Bromide | 10 g |
| Water to make | 1 liter |

TABLE 1

|  | Amount Added (g/mol Ag) | Developer (I) 20°C, 4 min. | | Developer (II) 35°C, 30 sec. | |
| --- | --- | --- | --- | --- | --- |
|  |  | Fog | Relative Sensitivity | Fog | Relative Sensitivity |
| Control | — | 0.04 | 100 | 0.21 | 76 |
| Compound (1) | 2.0 | 0.04 | 100 | 0.06 | 70 |
| Compound (2) | 2.0 | 0.04 | 100 | 0.04 | 64 |
| Compound (7) | 2.0 | 0.04 | 100 | 0.08 | 70 |
| Compound (10) | 2.0 | 0.04 | 100 | 0.06 | 70 |

TABLE 1-continued

| | Amount Added (g/mol Ag) | Developer (I) 20°C, 4 min. | | Developer (II) 35°C, 30 sec. | |
|---|---|---|---|---|---|
| | | Fog | Relative Sensitivity | Fog | Relative Sensitivity |
| Compound (17) | 2.0 | 0.04 | 100 | 0.14 | 78 |
| 1-Phenyl-5-mercapto-tetrazole (comparative compound) | 0.027 | 0.02 | 60 | 0.10 | 43 |

The above results clearly demonstrate that silver halide emulsions containing the additive of the present invention have reduced fog formation upon development at an elevated temperature using Developer (II) and not affected upon development using Developer (I).

EXAMPLE 2

A silver chlorobromoiodide emulsion containing 1.5 mol% of silver iodide, 0.5 mol% of silver chloride and 98 mol% of silver bromide was subjected to gold sensitization and sulfur sensitization. After adding thereto the same photographic additives as described in Example 1, the emulsion was divided into 10 equal portions. One portion was used as a control. To each of the remaining portions was added a compound shown in Table 2. The portions were coated and dried. The thus prepared samples were exposed and developed at 40°C for 30 seconds using the same Developer II as described in Example 1 to obtain the results set forth in Table 2.

TABLE 2

| | Amount Added (g/mol AgX) | Fog | Relative Sensitivity |
|---|---|---|---|
| Control | — | 0.38 | 100 |
| Compound (5) | 0.5 | 0.18 | 121 |
| | 2 | 0.05 | 100 |
| | 8 | 0.05 | 80 |
| Compound (12) | 0.5 | 0.25 | 115 |
| | 2 | 0.12 | 118 |
| | 8 | 0.05 | 95 |
| Compound (14) | 0.5 | 0.18 | 121 |
| | 2 | 0.07 | 107 |
| | 8 | 0.05 | 83 |

From the above results, it can be seen that the silver halide emulsions containing the compound of the formula (I) or (II) of the present invention show a remarkable anti-fogging action when developed in Developer (II) at an elevated temperature.

While the invention has been described in detail and with reference to specific embodiments thereof, it will be apparent to one skilled in the art that various changes and modifications can be made therein without departing from the spirit and scope thereof.

What is claimed is:

1. A photographic light-sensitive material comprising a support having thereon at least one silver halide photographic emulsion layer at least one of the layers of the photographic light-sensitive material containing in an amount sufficient to inhibit fog, a compound of the following general formulae (I) or (II):

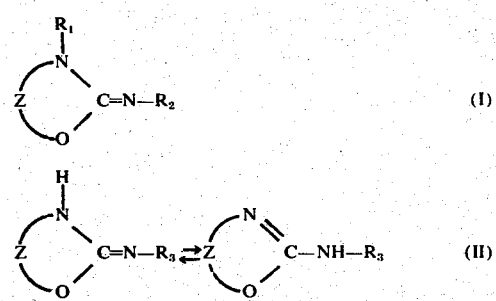

wherein $R_1$, $R_2$ and $R_3$ each represents a hydrogen atom, an alkyl group, an aryl group or a six member heterocyclic ring containing up to two nitrogen atoms with the remaining atoms of the six member ring being carbon atoms, or $R_1$ and $R_2$ can combine to form a ring through a dimethylene group or a methylene carbonyl group in which the methylene moiety can be substitued with an alkyl group having 1 to 4 carbon atoms or a phenyl group, and Z represents an alkylene group having 2 to 4 carbon atoms or the organic acid salts or mineral acid salts of the compound of the general formula (I) or (II).

2. The photographic light-sensitive material as claimed in claim 1, wherein said alkyl group $R_1$, $R_2$ or $R_3$ is an alkyl group containing 1 to 12 carbon atoms.

3. The photographic light-sensitive material as claimed in claim 1, wherein said alkyl group $R_1$, $R_2$ or $R_3$ is an alkyl group containing 1 to 6 carbon atoms.

4. The photographic light-sensitive material as claimed in claim 1, wherein said alkyl group $R_1$, $R_2$ or $R_3$ is a cycloalkyl group.

5. The photographic light-sensitive material as claimed in claim 1, wherein said alkyl group $R_1$, $R_2$ or $R_3$ is an aralkyl group, an aminoalkyl group or an alkoxyalkyl group.

6. The photographic light-sensitive material as claimed in claim 1, wherein said aryl group is a phenyl group, an alkyl-substituted phenyl group, an alkoxy-substituted phenyl group or an N,N-dialkylaminophenyl group.

7. The photographic light-sensitive material as claimed in claim 1, wherein said compound of the general formula (I) or (II) or the salts thereof is present in an amount of about 0.01 to 50 g per mol of silver halide.

8. The photographic light-sensitive material as claimed in claim 1, including at least one silver halide photographic emulsion layer and at least one other hydrophilic colloid layer.

* * * * *